(12) United States Patent
Marple et al.

(10) Patent No.: US 6,543,301 B2
(45) Date of Patent: Apr. 8, 2003

(54) IMPACTOR NOZZLE PLATE

(75) Inventors: Virgil A. Marple, Maple Plain, MN (US); Daryl L. Roberts, Blaine, MN (US)

(73) Assignee: MSP Corporation, Minneapolis, MN (US)

( * ) Notice: Subject to any disclaimer, the term of this patent is extended or adjusted under 35 U.S.C. 154(b) by 251 days.

(21) Appl. No.: 09/733,113

(22) Filed: Dec. 8, 2000

(65) Prior Publication Data

US 2002/0069709 A1 Jun. 13, 2002

(51) Int. Cl.$^7$ ................................................. G01N 1/24
(52) U.S. Cl. ....................................................... 73/863.23
(58) Field of Search .................. 73/28.01, 28.04–28.06, 73/863.22; 96/413

(56) References Cited

U.S. PATENT DOCUMENTS

| | | | |
|---|---|---|---|
| 2,538,116 A | 1/1951 | May ................................ 73/82 |
| 3,127,763 A | 4/1964 | Lippmann ........................ 73/28 |
| 3,518,815 A | 7/1970 | McFarland et al. ............ 55/241 |
| 3,693,457 A | 9/1972 | Pilat ................................ 73/28 |
| 3,938,366 A | * 2/1976 | Wertlake et al. ............ 73/28.06 |
| 4,133,202 A | 1/1979 | Marple ............................ 73/28 |
| 4,189,937 A | * 2/1980 | Nelson ........................ 73/28.06 |
| 4,274,846 A | 6/1981 | Smith ............................ 55/270 |
| 4,321,822 A | 3/1982 | Marple et al. ................... 73/28 |
| 4,391,151 A | 7/1983 | Nelson et al. ............ 73/863.23 |
| 4,400,982 A | 8/1983 | Bell .......................... 73/863.22 |
| 4,452,068 A | 6/1984 | Loo ................................ 73/28 |
| 4,463,595 A | 8/1984 | Yeh et al. ....................... 73/28 |
| 4,523,990 A | 6/1985 | Duyckinck .................. 209/138 |
| 4,570,494 A | 2/1986 | Dunn et al. .............. 73/863.22 |
| 4,640,140 A | 2/1987 | Burghoffer et al. ....... 73/863.22 |
| 4,725,294 A | 2/1988 | Berger .......................... 55/270 |
| 4,764,186 A | 8/1988 | Langer ............................ 55/17 |
| 4,827,779 A | 5/1989 | Marple et al. ............ 73/863.22 |
| 4,972,957 A | 11/1990 | Liu et al. ..................... 209/143 |
| 5,201,231 A | 4/1993 | Smith ....................... 73/863.22 |
| 5,343,767 A | 9/1994 | Marple et al. ........... 73/863.22 |
| 5,437,198 A | 8/1995 | John ......................... 73/863.22 |
| 5,693,895 A | 12/1997 | Baxter ..................... 73/863.22 |
| 6,240,768 B1 | * 6/2001 | Lemonnier ............... 73/863.22 |

FOREIGN PATENT DOCUMENTS

| | | |
|---|---|---|
| DE | 3110871 | 10/1982 |
| DE | 3545120 | 7/1986 |
| GB | 1354261 | 5/1974 |
| GB | 2179273 | 3/1987 |

\* cited by examiner

Primary Examiner—Robert Raevis
(74) Attorney, Agent, or Firm—Westman, Champlin & Kelly, P.A.

(57) ABSTRACT

A orifice plate used in an impactor that has a large number of very small openings therein is made of a thin material, and has a plurality of projections that extend outwardly from one surface thereof. The orifice plate is mounted adjacent a plate surface, and the projections serve to support the orifice plate spaced from the surface when the orifice plate deflects under differential pressures.

8 Claims, 2 Drawing Sheets

IMPACTOR NOZZLE PLATE

CROSS REFERENCE TO RELATED APPLICATIONS

Reference is made co-pending U.S. patent application Ser. No. 09/679,936, filed Oct. 5, 2000, for METHOD AND APPARATUS FOR CASCADE IMPACTOR TESTING, which is incorporated by reference.

BACKGROUND OF THE INVENTION

The present invention relates to a plate have orifices or nozzles therethrough used in particle classification impactors that classify particles according to size, and in particular relates to large plates used as part of the impactor or as a final filter where there are a large number of small nozzles or orifices. When the nozzles are very small the plate must be of a thin material. The nozzle plate has a selected number of dimples protruding from the surface that faces a surface to insure that a space is maintained between the plate and the surface through which exhaust fluid will flow after passing through the nozzles or orifices.

Cascade impactors that have relatively large diameter plates with small openings, are known in the field. Cascade impactors are illustrated in the co-pending U.S. Patent Application identified above.

In the final stages of a cascade impactor, particularly those used for analyzing dry powder inhalers, the particles that are being classified are relatively small, which requires small nozzles or orifices. Also a final filter can be provided which uses a thin plate with small openings. In order to have a nozzle plate that is effective with very small nozzles or orifices, the plate has to be thin, typically a few thousands of an inch. For large diameter plates that means the binding strength is relatively low, so when the nozzle plate is supported at its edges above a closely spaced impactor surface, the nozzle plate may bow under differential pressure caused by flow through the impactor. Such plates may. have as many as 2000 nozzles, and more may be needed in the future. The thin plate may bow enough to contact the impactor surface in the center portions of the nozzle plate, thereby reducing the number of effective orifices or nozzle openings and causing problems with appropriate flow and particle classification.

SUMMARY OF THE INVENTION

The present invention relates to impactor and filter plate contructions for cascade impactors where the plate is thin, and is supported at its peripheral edges above an impactor plate or a collection cup. Typically, a plurality of very small nozzle openings or orifices are formed in the nozzle or filter plate.

The plate of the present invention, which will be called a nozzle or orifice plate, has one or more small protrusions extending from the surface of the nozzle plate that faces a surface such as in a particle collector, cup or on an impactor plate. If the nozzle plate bows, the ends of the protrusions will contact the cup or plate surface and provide support for the nozzle plate at locations that are closely spaced enough to support the majority of the nozzle plate spaced from the cup or impactor plate surface. The protrusions insure that there is a passageway for a layer of air to flow between the nozzle plate and the impactor plate or cup.

In the preferred form, the protrusions are formed by dimpling the thin nozzle plate to form small projections from the surface of the plate that overlies the impactor plate or collection cup.

The use of the dimples is particularly helpful where there is a high differential pressure across the nozzle plate. Again, this is usually in connection with the later stages of a cascade impactor, or as part of a final filter.

Greater differential pressures are encountered in newer impactors, because of the requirements for relatively high air flows and small nozzles.

BRIEF DESCRIPTION OF THE DRAWINGS

FIG. 1 is a schematic representation of a cascade impactor, having a final impaction/filter stage using a nozzle plate made according to the present invention above a particle collection cup;

FIG. 3 is a fragmentary enlarged sectional view taken as on line 4—4 in FIG. 2.

DETAILED DESCRIPTION OF THE PREFERRED EMBODIMENTS

Figures 1, 3:
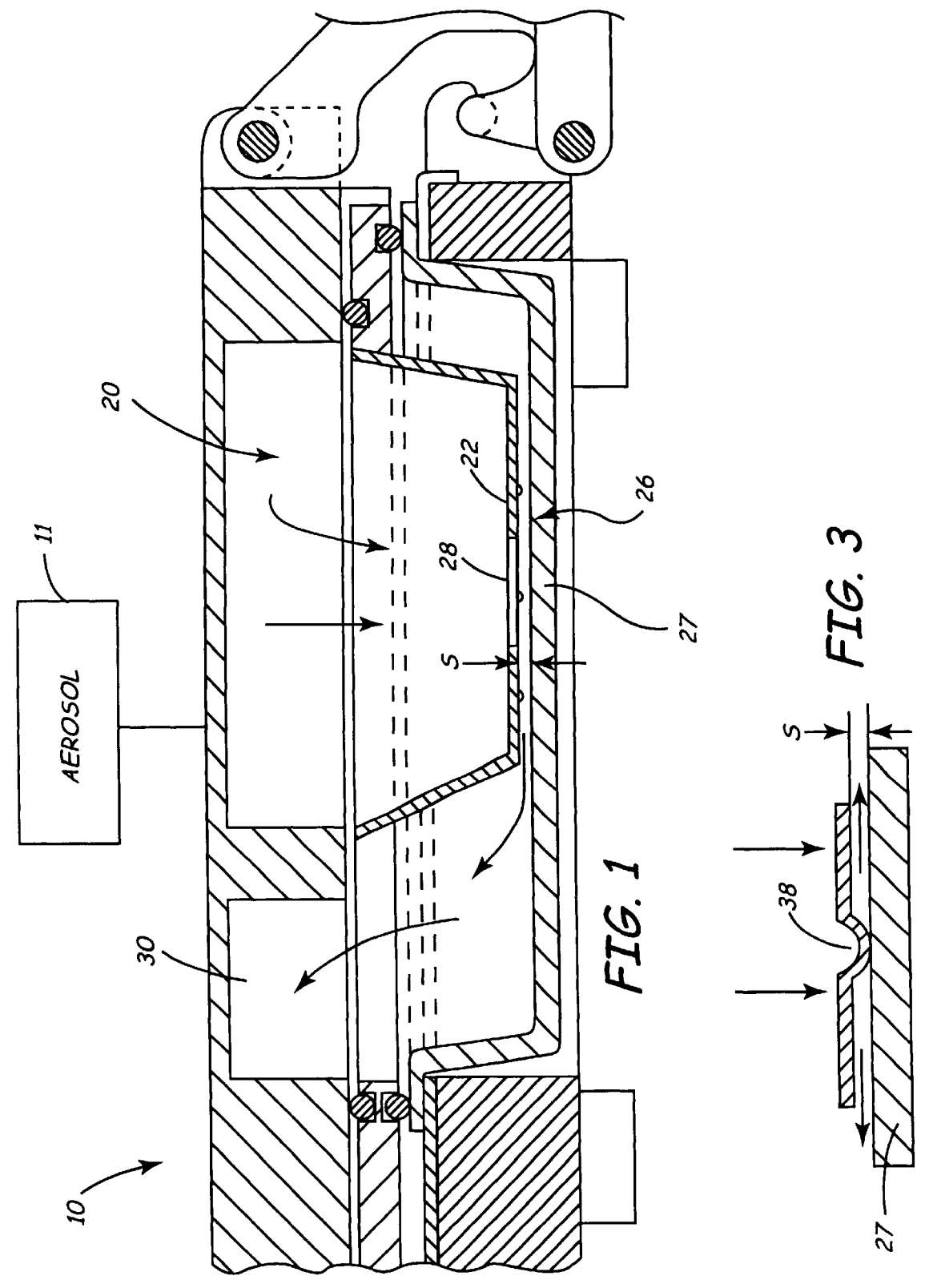
Figure 2:
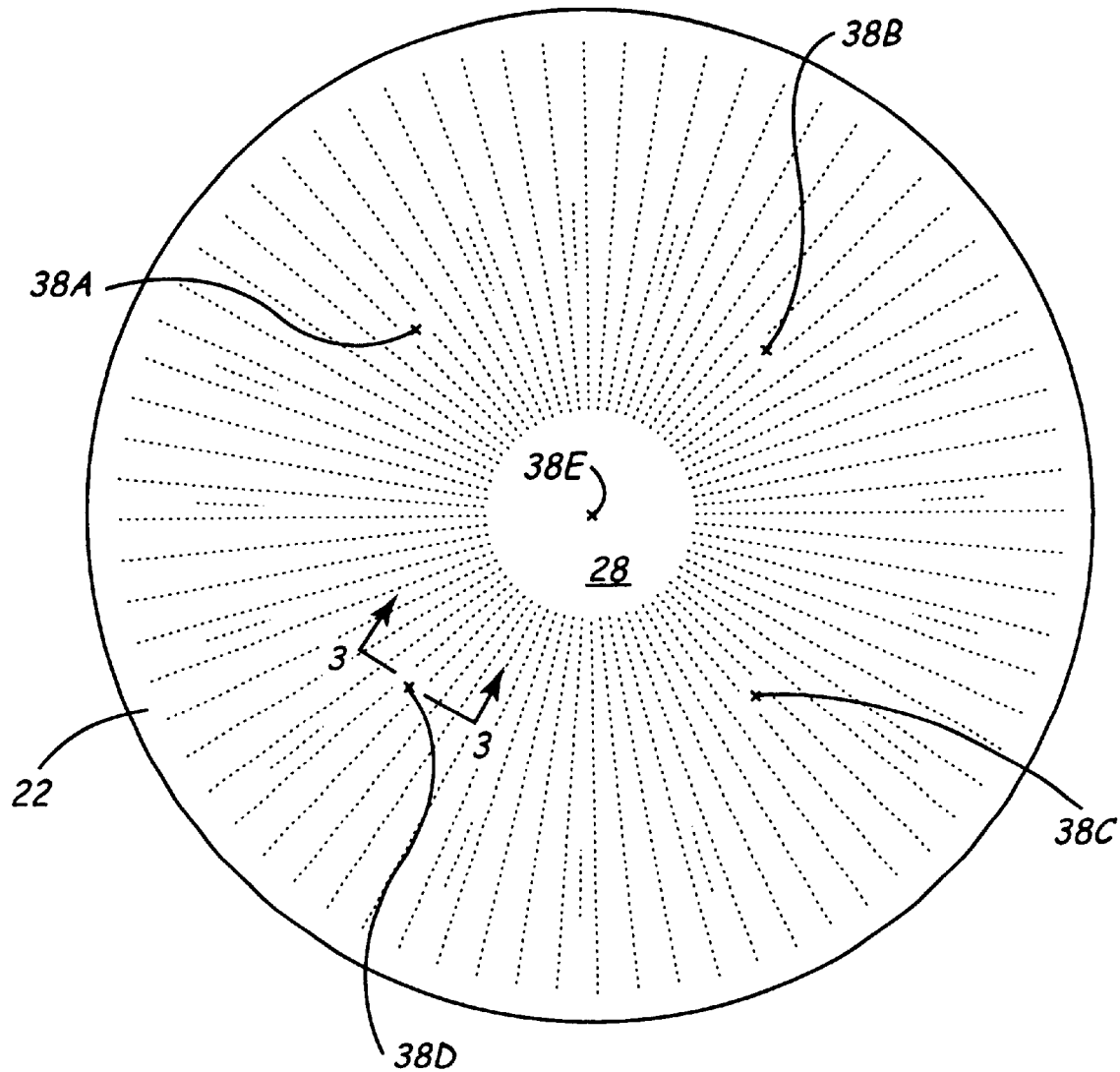
FIG. 2 is a plan view of the nozzle plate of the present invention.

FIG. 1. illustrates a cascade impactor that has a relatively large diameter nozzle plate as a final filter or impactor stage. This is a cascade impactor that has a series of individual impactors formed into a single device. Each impactor in the series is generally referred to as an impactor stage, with the impactor stages usually arranged in a descending order in particular size cut point, and therefore smaller and smaller nozzles or openings in the nozzle plates are used. The impactor 10, is provided with an aerosol, indicated as a source of aerosol 11, and the aerosol flows through a number of individual impactor stages, with descending order of openings or nozzle sizes.

The impactor 10 has input nozzles that directs the aerosol, which is a fluid containing the particles to be classified, onto impactor plates. A final stage of impaction, or a final filter stage is indicated schematically at 20. The final stage includes a nozzle plate or orifice plate 22 made according to the present invention, positioned above an adjacent surface of an impactor plate, as shown at the bottom wall of a particle collection cup 26. Fluid will discharge or exhaust fluid out a passageway 30 after passing through the nozzle plate. The nozzle plate 22 and impaction plate or collection cup 26 are supported in the cascade impactor housing 10 in a suitable manner. The nozzle plate 22 has a plurality of individual orifices or nozzles 23 that are arranged, as shown in FIG. 2, in radial patterns. The nozzles or orifices are small, for example, 70 microns in diameter. The nozzle plate has a central portion 28 that is not perforated.

The distance between the nozzle plate 22 and the bottom wall 27 of the cup 26 is represented at S, and is relatively small, so that at operating differentials in pressure, the nozzle plate 22 will bow until it touches the facing surface of the cup forming.

The flow from the impactor is discharged out through the passageway 30 and when the orifice or nozzle plate 22 bows to touch the cup bottom wall 27 flow through the nozzle or orifice plate will be impeded. The nozzle plate can nave a thickness of about 0.008 inches and as stated holes in the range of 70 microns in diameter. In any event the plate is generally less than 0.012 inches thick.

In order to prevent major portions of the nozzle plate from contacting the surface or wall 27, the nozzle plate has a series of dimples formed in it. As shown, five such dimples indicated at 38A, 38B, 38C, 38D and 38E in FIG. 3 are provided. These dimples, as illustrated in FIG. 3 are formed impressions or partial punch indentations that provide a protrusion below the general plane of the surface of the nozzle plate of approximately 0.50 millimeters. The dimples or protrusions are protruding in the direction of airflow as illustrated in FIG. 3. The small protrusions or dimples 38A–38E then will contact the surface of the cup or impactor plate to support the orifice plates sufficiently so that a gap will be maintained for airflow outwardly as indicated by the direction of the arrows in FIG. 3, and this flow then will be discharged out through the normal passageways indicated at 30 of the impactor.

The impactor shown in FIG. 1 is a cascade impactor that is formed into a generally flat frame, but cascade impactors with vertical stacking can use the same improvement as that disclosed to support orifice or nozzle plates that are made of thin metal and have small nozzles or orifices as required for operation of the impactors.

The protrusions can be made with a simple partial punch, to form the dimple. The protrusion provides a spacing of approximately 0.50 millimeters at the supported position shown in FIG. 3.

Also, as shown the area immediately surrounding the dimples is not perforated with the nozzles, but that region can be perforated if desired as well.

The support protrusions or projections can be formed with separate small pieces of material for spacing feet, if desired, but the method of partially punching or upsetting a portion of the material at selected locations on a thin orifice plate is easily carried out, and accommodates the necessary spacing desired.

Although the present invention has been described with reference to preferred embodiments, workers skilled in the art will recognize that changes may be made in form and detail without departing from the spirit and scope of the invention.

What is claimed is:

1. A thin orifice plate for a cascade impactor which has a plurality of openings therein of small diameter, and the plate tending to bow under differential pressures during normal operation relative to a surface adjacent to which the orifice plate is supported, said orifice plate having a selected number of known height protrusions extending from the orifice plate toward the surface, to provide support to prevent the orifice plate from contacting the surface at other than the locations of the protrusions during operation.

2. The nozzle plate of claim 1, wherein said protrusions are formed by dimpling the nozzle plate to provide projections extending toward the surface.

3. The nozzle plate of claim 1, wherein said nozzle plate has a plurality of openings arranged in a plurality of substantially radial rows.

4. The nozzle plate of claim 1, wherein the center portion of the nozzle plate is a continuous surface, without openings.

5. The nozzle plate of claim 4, wherein said center portion has at least one projection therein.

6. The nozzle plate of claim 1, wherein said nozzle plate has a circular periphery.

7. The nozzle plate of claim 1, wherein the projections support the nozzle plate to be spaced substantially at least 0.50 millimeters.

8. The nozzle plate of claim 1, wherein the nozzle plate has a thickness of under 0.012 inches.

* * * * *